(12) United States Patent
Fontes et al.

(10) Patent No.: US 7,649,017 B2
(45) Date of Patent: Jan. 19, 2010

(54) COMPOSITIONS INTENDED FOR THE TREATMENT OF PERIPHERAL NEUROPATHIES, PREPARATION THEREOF AND USES OF SAME

(75) Inventors: Michel Fontes, Fuveau (FR); Edith Passage, Marseilles (FR); Veronique Sanguedolce, Aix en Provence (FR); Jean-Chretien Noreel, Marseilles (FR)

(73) Assignees: Universite de la Mediterranee, Marseille Cedex (FR); Institut National de la Sante et de la Recherche Medicale, Paris Cedex (FR); Association Francaise Contre les Myopathies, Paris Cedex (FR)

( * ) Notice: Subject to any disclaimer, the term of this patent is extended or adjusted under 35 U.S.C. 154(b) by 344 days.

(21) Appl. No.: 10/521,239

(22) PCT Filed: Jul. 15, 2003

(86) PCT No.: PCT/FR03/02236

§ 371 (c)(1),
(2), (4) Date: Apr. 14, 2005

(87) PCT Pub. No.: WO2004/006911

PCT Pub. Date: Jan. 22, 2004

(65) Prior Publication Data

US 2005/0187290 A1    Aug. 25, 2005

(30) Foreign Application Priority Data

Jul. 16, 2002  (FR) ................................. 02 08966

(51) Int. Cl.
*A01N 43/08* (2006.01)
*A61K 31/34* (2006.01)
(52) U.S. Cl. ..................................... 514/474
(58) Field of Classification Search .................. 514/474
See application file for complete search history.

(56) References Cited

U.S. PATENT DOCUMENTS 6,114,388 A        9/2000  Geffard
6,486,190 B1 *    11/2002  Cupps et al. ................. 514/394
2002/0198236 A1 * 12/2002  Baxter et al. ................ 514/324

FOREIGN PATENT DOCUMENTS

| EP | 0 694 302 A1 | 1/1996 |
| EP | 0 797 993 A1 | 10/1997 |
| EP | 0 820 770 A2 | 1/1998 |
| GB | 890638 | 3/1962 |
| WO | 95/01096 | 1/1995 |

OTHER PUBLICATIONS

Pomerance et al. Journal of Biological Chemistry, 2000. vol. 275, No. 51, Issue of Dec. 22, pp. 40539-40546.*
Djoneidi et al. Gene. 2000. vol. 248, pp. 223-231.*
Austria et al. Journal of Pharmaceutical and Biomedical Analysis. 1997. vol. 15, pp. 795-801.*
Fujinami etal. Chemical and Pharmaceutical Bulletin. 2001, vol. 49, Issue 5, pp. 642-644.*
K. Matsushita et al., "Experimentally-induced toxic effects in the retina upon the regeneration of visual purple", XP002236327.
M. Giubileo, "A case of Guillain-Barre syndrome in a worker exposed to lead", XP002236328.
P. Viktora, "Treatment of Landry's ascending type of polyradiculoneuritis in a resuscitation department", Bratislavske Lekarske Listy 1973, pp. 731-733.
H. Wang et al., "Experimental and clinical studies on the reduction of erythrocyte sorbitol-glucose ratios by ascorbic acid in diabetes mellitus", Diabetes Research and Clinical Practice, vol. 28, No. 1, 1995, pp. 1-8.
U. Grober, "Orthomolecular medicine: Usefulness of micronutrients in diabetes mellitus", Deutsche Apotheker Zeitung, Feb. 14, 2002, Germany, vol. 142, No. 7, pp. 46-52.
International Search Report of PCT/FR03/02236 dated Dec. 22, 2003.
Matsushita et al. "Experimentally-induced toxic effects in the retina upon the regeneration of visual purple" AN 62-46556, Nippon Ganka Gakkei Zasshi (1962), 66(9), 687-94 (English Abstract).
Giubileo "A case of Guillain—Barre syndrome in a worker exposed to lead" Med. Iavoro (1955), 46, 162-6 (English abstract).

* cited by examiner

*Primary Examiner*—Sreeni Padmanabhan
*Assistant Examiner*—Samira Jean-Louis
(74) *Attorney, Agent, or Firm*—Nixon & Vanderhye P.C.

(57) ABSTRACT

The invention relates to the technical fields of biology, pharmacology and medicine. The invention is suitable for use in particular in the human and animal health fields. More specifically, the invention relates to the use of a cAMP modulator in the preparation of compositions that are intended for the prevention or treatment of peripheral neuropathies. The invention further relates to tools and kits to prepare the aforementioned compositions.

4 Claims, 3 Drawing Sheets

Figure 1:
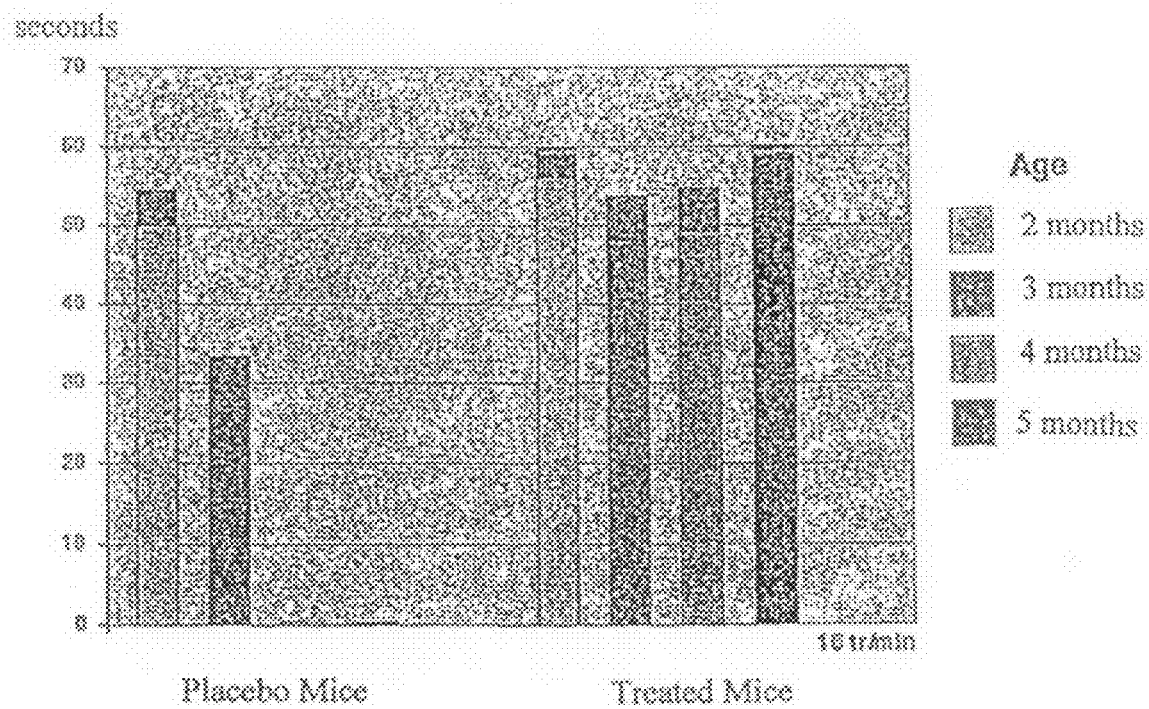

COMPOSITIONS INTENDED FOR THE TREATMENT OF PERIPHERAL NEUROPATHIES, PREPARATION THEREOF AND USES OF SAME

This application is the US national phase of international application PCT/FR2003/002236 filed 15 Jul. 2003 which designated the U.S. and claims benefit of FR 02/08966, dated 16 Jul. 2002, the entire contents of each of which are hereby incorporated by reference.

INTRODUCTION AND STATE OF THE ART

The invention relates to the technical fields of biology, pharmacology and medicine. The invention is suitable for use in particular in the human and animal health fields. More specifically, the invention relates to the use of a cAMP modulator in the preparation of compositions that are intended for the prevention or treatment of peripheral neuropathies. The invention further relates to tools and kits used to prepare the aforementioned compositions.

Neuromuscular diseases encompass all disorders which affect the cells and fibers of the peripheral nervous system (neurogenic disorder), which affect the muscles (myogenic disorder), or which affect the junction between nerve fibers and muscle fibers (disease of neuromuscular transmission). Among the neuromuscular diseases, the term neuropathies is reserved for disorders of the nerve fibers resulting in neuronal destruction.

Neurogenic disorders can be divided into three subgroups according to the functional type of nerve fiber or cell involved:

Pure motor neuron disorders, for example the spinal muscular atrophies. These are related to abnormalities of the motor neurons in the peripheral nervous system (PNS). Other pure motor neurogenic disorders exist in which the motor neurons are normal, but the motor fibers of nerves are specifically damaged.

Pure sensory neuron disorders affect the sensory fibers of nerves in the peripheral nervous system.

Sensorimotor or sensitivomotor neuropathies involve motor and sensory nerves. These neuropathies are by far the most common.

Sensorimotor neuropathies may not have a hereditary component or in contrast may be hereditary as in Charcot-Marie-Tooth (CMT) disease.

CMT, first described in 1886, is the most common hereditary sensorimotor neuropathy. Several CMT types may be distinguished: types I and II are usually autosomal dominant disorders but transmission may also be autosomal recessive. More rarely, type I disease is inherited as an X-linked trait.

CMT disease thus displays wide genetic heterogeneity, although in 1991 it was shown that the majority of patients with the most common form of CMT—type 1A (more than half of cases)—have a duplication of region 17p11.2 [Lupski, 1991 #1] [Raeymaekers, 1991 #2], of invariant size (1.5 Mb), which comprises the gene coding for the myelin protein PMP22. Point mutations found in the rare CMT IA patients without this duplication have made it possible to show that this gene is the principal cause of the CMT 1A phenotype.

The time of onset of the earliest symptoms is highly variable from one patient to another and for each type of CMT disease. Likewise, the extent to which the gene underlying the disease is expressed depends on several factors. Thus, within a same family, disease severity may differ between family members. Several different components of the peripheral nervous system may be affected. A classification of these diseases has been proposed which is based on the involved components:

CMT type I is characterized by abnormalities of the myelin sheaths, which are often very thin and sometimes totally absent. The process leading to the loss of myelin is called demyelination. When the myelin sheath is damaged, saltatory conduction of the nerve impulse can no longer take place correctly and the nerve conduction velocity is slowed. Sometimes, the nerve impulse no longer arrives at all. This occurs in particular for the longer axons, namely, those reaching the extremities of the body (distal parts) and innervating the feet and hands. This is why these CMT diseases manifest preferentially in the limbs and in particular at the extremeties thereof.

When demyelination occurs, repair of the myelin sheath can take place (remyelination). These alternating phenomena of demyelination and remyelination can lead to the gradual formation of concentric structures having the microscopic appearance of an onion bulb. In these onion bulbs the number of Schwann cells surrounding the axons is markedly increased, the nerve fibers therefore become hypertrophic.

In CMT type II disease, the abnormality is located in the axons themselves. As the number of axons decreases (axonal degeneration), so does the number of nerve fibers. Sometimes, regeneration of the damaged axons can occur. This phenomenon is called axonal budding.

In CMT type I, nerve conduction velocities are sharply slowed. In CMT type II, abnormalities of nerve conduction velocities are minor or absent.

The age at onset of CMT type I and type II in humans can range from the first to the sixth decade of life. CMT type II usually presents later than type I, rarely before age 10. However, it is usually impossible to distinguish these two CMT types on the basis of clinical symptoms alone.

Irrespective of age at onset, the first abnormalities concern the most distal parts of the body, namely the feet (pes cavus) and toes. If the disease progresses, the anterior and external leg muscles are affected, producing atrophy (in particular this is referred to as "stork legs"), and sometimes the muscles of the hands. In the latter case, fine finger movements and movements requiring both strength and precision become difficult. In some cases, the thigh, shoulder and back muscles are eventually involved. Tremor is present fairly often, due to the extra muscle work demanded of muscles weakened by the disease. In all cases, the disease progresses slowly and gradually over a period of years, or sometimes not at all. Regardless of which part of the body is affected, the involvement is always symmetrical.

As with most neuromuscular diseases, in particular the hereditary diseases, it is not currently possible to cure CMT and so far no curative therapy has been proposed, the only treatments available to patients being symptomatic to relieve as far as possible the unpleasant effects of the disease. Among the medicaments used to treat symptoms, quinine derivatives are used for muscle cramps. When the usual analgesics (aspirin, paracetamol, etc.) are ineffective, pain can sometimes be managed by medicaments such as certain antidepressants or antiepileptics. Surgery can also be considered to correct bone-joint deformations causing pain and discomfort.

Alongside CMT types I and II, there exist other hereditary diseases which produce some of the same symptoms described for CMT, associated with other abnormalities. Particular examples include hereditary neuropathies with nerve pressure palsies, Refsum's disease, Strumpell-Lorrain disease, retinitis pigmentosa, etc.

The present invention proposes for the first time compositions and methods for the prevention and treatment of peripheral neuropathies, whether hereditary or not. This is accomplished in a surprising manner by the administration of compositions comprising at least one modulator of cAMP, such as vitamin C for example.

Ascorbic acid, or vitamin C, has many beneficial effects and the use thereof is widely recommended as a part of various therapeutic treatments. Some of the known biological actions of vitamin C are explained by its antioxidant action, which helps fight against free radical damage. It also participates in the synthesis of neurotransmitters secreted by the brain and by nerve terminals. A particular example of the latter is the catecholamines which play a role in stress reactions. Vitamin C is also necessary for muscle and bone development and good health. It accelerates healing processes, aids in immune system functioning (hence its widespread anti-infective use), fights allergic reactions, intervenes in hormone synthesis and in iron absorption. It plays a role in detoxification by stimulating the production of an enzyme, cytochrome P450. It also counteracts the action of the carcinogenic nitrosamine compounds. Vitamin C is used, for example, to promote collagen regeneration, to fight against bacterial or viral diseases or to fight against the problems related to atherosclerosis, hypertension, hemorrhoids or diabetes. It is also used to regulate digestion.

The invention now describes a novel, particularly advantageous use of cAMP modulators and in particular of vitamin C in the preparation of pharmaceutical compositions intended for the prevention or treatment of peripheral neuropathies.

GENERAL DESCRIPTION OF THE INVENTION

The problem that the invention proposes to resolve is that of offering affected patients or subjects at risk of developing a peripheral neuropathy compositions intended for the prevention or treatment of said neuropathies.

A first particular aspect of the invention thus concerns the use of a cAMP modulator for preparing a composition for preventing or treating peripheral neuropathies. An example of a particularly advantageous cAMP modulator in the context of the invention is vitamin C as well as any derivative thereof. In fact, vitamin C behaves like a cAMP inhibitor. A particularly preferred aspect of the invention thus concerns the use of a cAMP inhibitor for preparing a composition intended for the prevention or treatment of peripheral neuropathies.

Another aspect of the invention relates to a method for preparing a composition for treating peripheral neuropathies characterized in that the composition comprises, as active substance, a cAMP modulator, such as ascorbic acid or a derivative thereof that can be assimilated by humans or animals, in association with a pharmaceutically acceptable vehicle.

The invention also relates to a method for the preventive or curative treatment of peripheral neuropathies, comprising administering to a subject affected by or presenting a risk of developing such pathology, an effective amount of cAMP inhibitor and for example of vitamin C or a derivative thereof.

The invention further concerns a kit for practicing an inventive method.

DETAILED DESCRIPTION OF THE INVENTION

The invention thus concerns the use of a cAMP modulator and/for example of vitamin C or a derivative thereof for preparing a composition intended for the prevention or treatment of peripheral neuropathies.

The peripheral neuropathies at issue are hereditary or non-hereditary neuropathies. A particular object of the invention thus concerns the use of a cAMP inhibitor and in particular the use of vitamin C, for preparing a composition intended for the prevention or treatment of hereditary peripheral neuropathies, preferably demyelinating neuropathies and in particular Charcot-Marie-Tooth disease, but also of hereditary neuropathies of the type which cause nerve pressure palsies, Refsum's disease, Strumpell-Lorrain disease, retinitis pigmentosa, and the like. According to another preferred embodiment of the invention, the inventive composition is intended for the prevention or treatment of non-hereditary peripheral neuropathies such as neuropathies caused by a treatment such as hemodialysis, diabetic neuropathies, but also neuropathies such as acute polyradiculoneuropathy, chronic polyradiculoneuropathy, Guillain-Barré syndrome, and the like.

Without intending to make a link to any particular theory regarding the mechanism of action of vitamin C, the observations made by the inventors in the scope of their work allowed them to advance different hypotheses. The inventors recently showed that expression of the PMP22 gene coding for a myelin sheath protein is under the direct control of cAMP, via CREB binding to two sites in the gene promoter, located 1.5 kb from the transcription initiation site. In the absence of cAMP, the activity of the schwann specific minimal promoter (300 bp) is inhibited. Treatment with cAMP removes this inhibition and restores expression of the minimal promoter. One of the hypotheses considered by the inventors was that use of an amount of cAMP which on the contrary is reduced could reduce the activity of this promoter and thus reduce overexpression of PMP22. The inventors furthermore noted that the severity of the phenotype appeared to depend on the level of overexpression, with a threshold effect. In fact, 70% overexpression does not appear to be pathogenic whereas 100% overexpression (CMT IA patients) does. In the scope of the invention, the inventors tested the action of vitamin C on the endogenous cAMP pool and found that reduction of said pool led to a decrease in PMP22 expression, so that the level thereof fell below the pathogenic threshold. This hypothesis was validated in animals treated for 3 months with a cAMP inhibitor, namely, vitamin C, and in animals from the same litter to which a placebo was administered. These animals were sacrificed. The sciatic nerves were harvested, RNA was extracted and the level of expression was measured by real time PCR, with the help of primers specific for the human transcript. The results show that the level of PMP22 expression decreased after vitamin C treatment. The sciatic nerve of treated mice thus contained 8 times less PMP22 messenger RNA than that of mice in the placebo group (see Materials and Methods).

More particularly, then, the invention relates to the use of a cAMP modulator and for example the use of vitamin C or a derivative thereof for preparing a composition capable of regulating the expression of cAMP and/or the expression of the PMP22 protein which is part of the myelin sheath surrounding nerve fibers. According to a preferred embodiment of the invention, the inventive composition decreases the expression of cAMP and/or that of the PMP22 protein which is generally overexpressed in subjects with peripheral neuropathies, in particular in subjects suffering from CMT type I disease.

The invention further concerns a method for preparing a composition intended for the treatment of peripheral neuropathies characterized in that the composition comprises, as active substance, a cAMP inhibitor, for example ascorbic acid or a derivative thereof, that can be assimilated by humans or animals, in association with a pharmaceutically acceptable vehicle.

In the context of the aforementioned uses and methods, vitamin C is selected in the group consisting of natural vitamin C, synthetic vitamin C and a mixture thereof. Natural vitamin C can be extracted from a natural product and in particular from products such as acerola, the wild rose berry, guava, parsley, blackcurrant, kiwi fruit, fennel, papaya, raw cauliflower, cooked broccoli, orange, watercress, red cabbage, potato, mango, lemon and grapefruit juice, redcurrant, raspberry, passion fruit, blueberry, etc. or else products artificially enriched in vitamin C. It is also possible to use a vitamin C derivative such as vitaimn C esters or vitamin C salts. In particular, vitamin C esters can be ose esters of ascorbic acid, such as in particular glycosylated, mannosylated, frucotsylated, fucosylated, galactosylated, N-acetylglucosaminated, N-acetylmuramic derivatives of ascorbic acid and their mixtures and more specifically ascorbyl-2 glucoside or 2-O-alpha-D-glucopyranosyl ascorbic acid or else 6-O-beta-D-galactopyranosyl L-ascorbic acid. These latter compounds and their methods of preparation are described in particular in documents EP-A-487404, EP-A-425066 and J05213736. Vitamin C esters can also be esters such as ascorbyl palmitate or L-ascorbate dipalmitate. Other vitamin C derivatives that can be used in the scope of the invention are metal salts of phosphorylated ascorbic acid, such as in particular the alkaline metal ascorbyl phosphates, the alkaline earth metal ascorbyl phosphates and the transition metal ascorbyl phosphates. Magnesium ascorbyl phosphate is advantageously used. They can also be ascorbyl sulfates.

The invention also relates to a method such as described hereinabove characterized in that the composition is a dietary supplement adapted to animal consumption, preferably to human consumption.

The invention also concerns a method of preventive or curative treatment of peripheral neuropathies, comprising administering to a subject presenting with or at risk of developing such pathology, an effective amount of a cAMP inhibitor, for example of vitamin C or a derivative thereof. A particularly interesting advantage of this method of treatment is that it can use as active substance a molecule, vitamin C, which is low cost, easy to obtain and directly usable in phase III clinical trials.

In fact, the compositions used in the inventive methods comprise, as active substance, a cAMP modulator, preferably a cAMP inhibitor, for example ascorbic acid or a derivative thereof in association with a pharmaceutically acceptable vehicle. They are intended to prevent or treat a peripheral neuropathy. Such composition may be a pharmaceutical composition or a dietary supplement adapted to animal consumption, preferably to human consumption. The inventive composition generally comprises between 250 mg and 6 grams of ascorbic acid or a derivative thereof, preferably between 1 g and 6 grams, even more preferably between 3 and 5 grams.

The amount of active ingredient to be administered in the treatment of peripheral neuropathies according to the invention obviously depends on the nature and severity of the disorder to be treated and on the weight of the patient. Nonetheless, preferred unit doses will generally comprise from 250 mg to 6 grams of vitamin C, advantageously from 1 to 6 grams, even more preferably from 3 to 5 grams. These amounts do not rule out the intake of larger amounts of vitamin C or vitamin C derivatives. In fact, vitamin C is a well-known molecule and its side effects, which are few, are also known (lithiasis in particular). Vitamin C is traditionally thought to promote the formation of renal calculi (oxalate type) due to its catabolic transformation to oxalate and due to acidification of the urine. However, cohort studies ("*The health effect of vitamin C supplementation: a review*". Bendich et al., J Am Coll Nutr, 1995, 14, 124-136; "*No contribution of ascorbic acid to renal calcium oxalate stones.*" Gester H, Ann Nutr Metab, 1997, 41, 269-82; "*Biomarkers for establishing a tolerable upper intake level of vitamin C.*" Johnston C S. Nutr Rev, 1999, 57, 71-7; CURHAN G C, WILLETT W C, RIMMEB et al., "*A prospective study of the intake of vitamins C and B6 and the risk of kidney stones in men.*" The Journal of Urology, 1996, vol 155: 1847-1851; CURHAN G C, WILLET W C, SPEIZER F E et al., "*Intake of vitamins B6 and C and the risk of kidney stones in women.*" J Am Soc Nephrol, 1999, 10: 840-845; GERSTER H, "*No contribution of ascorbic acid to renal calcium oxalate stones*". Ann Nutr Metab, 1997, 41: 269-282) have shown that daily doses of up to 1500 mg of vitamin C do not increase the risk of kidney stones. Some publications report intake of very high oral doses on the order of 20 to 40 grams without any particular effect. The pharmacokinetic profile of ascorbic acid explains why high doses of this active substance do not increase toxicity nor the risk of kidney stones. In fact, gastrointestinal absorption occurs through a sodium-dependent transporter and is saturable. For 1 gram of vitamin C, 75% is absorbed. For 5 grams, 20% is absorbed. In addition, metabolic transformation of ascorbic acid to oxalate is a minor phenomenon: 1% of urinary ascorbic acid is metabolized to oxalate (Campbell G. D., Steinberg M. H., Bower J. D., "*Ascorbic acid-induced hemolysis in G-6-PD deficiency*", Ann Inter Med, 1975, 82(6), 810; Rees D. C., Kelsey H., Richards J. D. M., "*Acute haemolysis induced by high dose ascorbic acid in glucose-6-phosphate dehydrogenase deficiency*", Br J Med 1993, 306, 841-2). Thus, quantities far higher than those described previously can be absorbed without risk by humans or animals.

The unit doses will normally be administered once a week, but shorter dosing intervals are also possible, for example every 2 or 3 days or 1 to 5 times per day. In this case, the unit doses typically comprise from 0.1 to 1 g of vitamin C. According to a preferred embodiment, the administered doses can correspond to administration of approximately 250 mg per day for 6 days followed by administration of 5 grams (two 2.5-gram tablets for example) on the seventh day. The use of vitamin C in the treatment of peripheral neuropathies is preferably for a prolonged period. Such administration generally takes place over long treatment cycles that can be repeated during the patient's lifetime. The treatment cycle may be several months, preferably from two months to six months. In the most severe cases, administration of vitamin C can be continued for several years, even for the patient's entire lifetime.

Ascorbic acid or derivatives thereof can be taken without food (before or after meals) or during meals. The administration of an inventive composition based on vitamin C is preferably by the oral route. Nevertheless it can also take place by the enteral or parenteral route in a suitable vehicle. Vitamin C is in a form (solid or liquid) which is suited to such administration. In fact, vitamin C is a light-sensitive molecule and easily oxidizable in particular in aqueous medium. On the other hand, in anhydrous medium, it has considerably less solubility.

The vitamin C used in the present invention is advantageously in solid form. In the case of ascorbic acid salts, they are preferably administered in soluble form with water or any other beverage. Water-compatible alcohols such as propylene glycol, polypropylene glycol and glycerol have been used as vehicles capable of increasing the stability of vitamin C in water [see U.S. Pat. No. 4,983,382 (Wilmott and Znaiden)] and can also be used in the scope of the invention.

The vitamin C can thus be in the form of aqueous solutions containing the aforementioned unit doses, in an alcohol type vehicle or else in an isotonic or sterile vehicle that optionally contains dispersives and/or softeners which are pharmacologically compatible. It is also possible to administer vitamin C in association with other compounds capable of potentiating its action, such as buffered solutions or derivatives. Said compositions are formulated in a suitable manner (capsule, injectable solution, tablet, etc.) for oral, enteral or else parenteral administration, for example intravenous, intramuscular or subcutaneous administration, introduction in an intravenous infusion set or at the surface of a dialysis membrane, or else administration by an implant system allowing subcutaneous diffusion.

The inventive compounds can also be administered by the rectal or percutaneous route. In this case, the unit dose forms are prepared in the conventional manner according to classical methods known to those skilled in the art, with the excipients commonly used in this field.

Regardless of the chosen route of administration, preferred compositions based on vitamin C according to the invention have a form which is favorable to the protection and optimal assimilation of the active substance.

The invention also relates to tools and kits intended for practicing one of the methods such as described hereinabove.

The advantageous properties of vitamin C in the treatment of peripheral neuropathies are illustrated in the next section by pharmacological data and examples, which are given for purposes of illustration and not by way of limitation.

LEGENDS OF FIGURES

FIG. 1: Two-month-old males from two litters were treated with either placebo (4 animals) or with vitamin C (6 animals) for 3 months. Rotor-Rod test performance was evaluated every month (at 3 months, 4 months and 5 months). The standard deviation is indicated by the darkened section at the top of each column.

Figure 2:
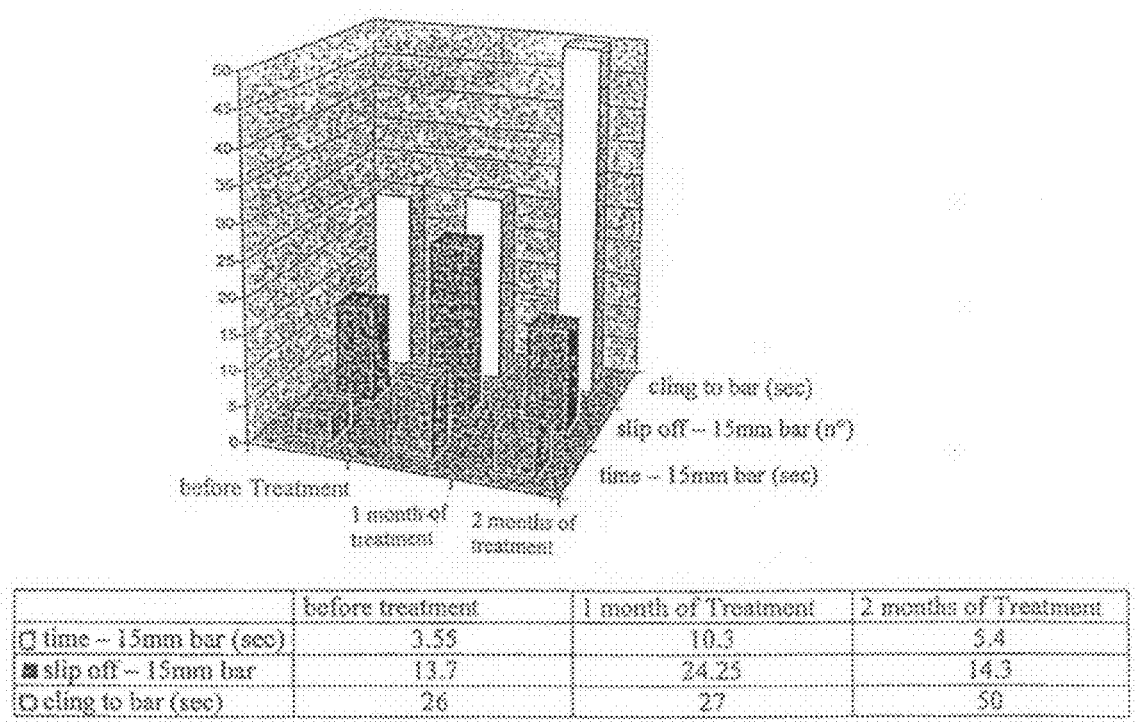

FIG. 2: A second series of preclinical tests with the same design as the first series (described in FIG. 1) was carried out. Animals were tested after one month and two months of treatment using the bar crossing test (the longer the animal takes to cross the bar or the more it slips off, the worse the locomotor performance). Animals were also tested in the grip test which measures the traction strength that must be applied for the animal to release the bar (the higher this value the better the performance).

Figure 3:
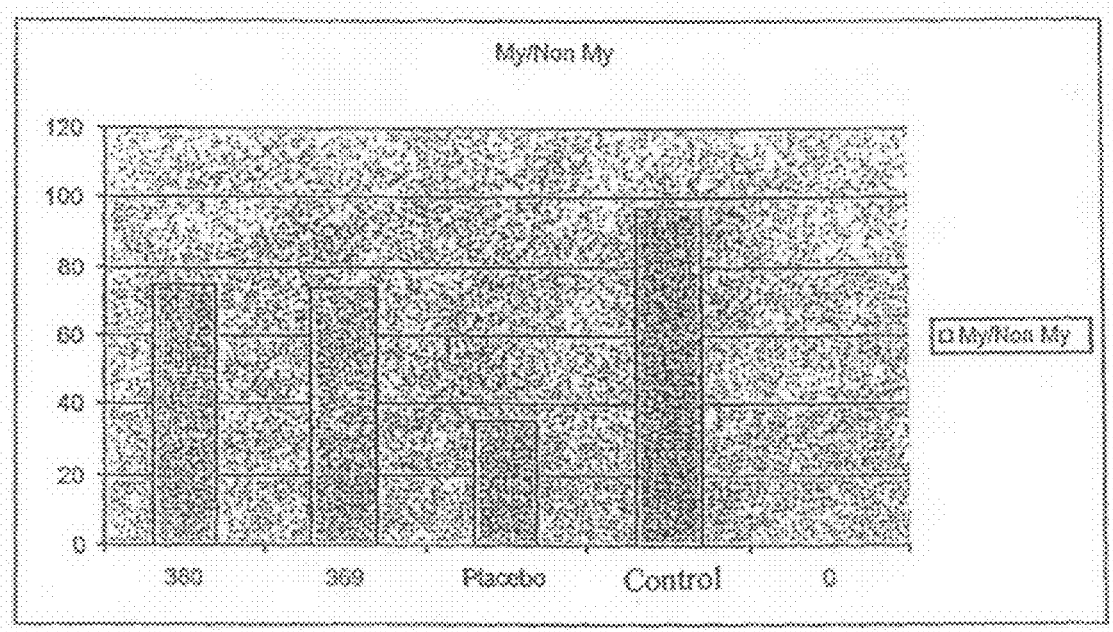

FIG. 3: Animals were treated with vitamin C for three months (369 and 380) or with placebo, then sacrificed. The sciatic nerve was harvested and the percentage of myelinated fibers was determined by histologic analysis and is given in the figure on the ordinate, together with the results of a non-transgenic control (more than 95% of peripheral nerve fibers are myelinated in adults).

MATERIALS AND METHODS

Charcot-Marie-Tooth disease (CMT) is the most common hereditary peripheral neuropathy, affecting one in 2500 individuals.

To better understand the pathophysiology of this disease and to propose therapeutic solutions, a murine disease model was constructed in 1996 by transgenesis of a human YAC containing the PMP22 gene (Huxley et al., Human Molecular Genetics, 1996, Vol. 5, No. 5, 563-569). Studies in this model have demonstrated its relevance to the human disease (Huxley et al., Human Molecular Genetics, 1998, Vol. 7, No. 3, 449-458). The action of vitamin C was tested in this model.

A first "open" trial was carried out, without inclusion criteria, by simply separating males and females so as to rapidly determine whether a phenotypic correction effect could be seen. The Rotor-Rod test, classically used in pharmacology, was chosen as the criterion of muscle strength. Sixteen females and 12 male transgenic C22 animals were tested as untreated controls (results given in Table I).

TABLE I

| | Untreated animals | | Treated animals | |
|---|---|---|---|---|
| | Number of animals | Seconds on the bar | Number of animals | Seconds on the bar |
| Males | 12 | 11.3 +/− 13 | 5 | 46 +/− 14 |
| Females | 16 | 25 +/− 8 | 12 | 45.7 +/− 10 |
| Non Transgenic | 20 | 60 | | |

Twelve C22 females and 5 males were treated with vitamin C. The results, expressed in seconds, confirm that males were more severely affected (males in this line even have early mortality, since all males die before 10 months of age). Furthermore, it was clearly seen that Rotor-Rod test performances in both treated males and treated females were clearly superior to those of untreated animals. The correction appears partial, at least in this study, because both the males and females had a similar and slightly inferior performance than the controls.

These initial, very encouraging results led to a second series of studies, conducted like a human clinical trial, that is, double-blind (vitamin C versus placebo).

Only males (from two litters) were used, since the degree of severity is sex-specific. Half the males were treated with a placebo and the other half with vitamin C at a dose of 1.12 mg once a week. The fact that only males were included is very important, because it is known that severity varies widely in human patients according to sex, a variability also seen in the animal models used, in which there appears to be a major modifier gene having an impact on myelination. "Genetic background" thus seems to play a significant role in the severity of the phenotype. It was therefore justified to work with individuals from a same litter.

Starting at 2 months of age (the pathological locomotor phenotype appears at about 1 month of age), the animals were treated by gavage with 1.12 mg per week of either vitamin C or placebo. The animals were then evaluated in the Rotor-Rod test. The study lasted for three months (age of animals: two to five months). The results are illustrated in FIG. 1.

These results show that the first month of treatment was not very effective, even though Rotor-Rod test performance decreased less in treated animals than in controls. On the other hand, a dramatic improvement was seen starting from the second month of treatment: treated animals stayed for almost 50 seconds on the bar, whereas untreated animals could not stay on at all (litters with a severe phenotype had been selected). The animals' performance further improved during the third month.

In light of these spectacular findings, the vitamin C treatment was continued and the animals' performance was observed. Performance continued to improve, even after taking into account that the animals had aged. Furthermore, animals that had not been sacrificed (see below) were still alive at age 24 months, thereby indicating that the lethal phenotype in males had been corrected.

To confirm these findings and further investigate the mechanism of phenotypic correction, a third study was carried out. Two tests were used: a posture test (crossing a bar that gets progressively narrower) and a test of muscle strength, the "grip test". FIG. 2 illustrates the results after two months of treatment. It clearly appears that bar crossing performance deteriorated at the first month, then improved during the second, in full agreement with the Rotor-Rod results. As for the grip test, improvement was also seen starting from two months of treatment. This test is a good indicator of muscle strength. The results therefore confirm that vitamin C promotes a recovery of muscle strength, probably by reacquisition of functional muscle.

To obtain data on the mechanism of this phenotypic correction, the histologic features of the nerves of treated animals were studied. For this, some of the treated animals were sacrificed and a histologic analysis was performed. The percentage of myelinated nerve fibers increased with treatment (FIG. 3). This percentage was 95% for non-transgenic animals, 20-30% for untreated C22 mice and 70% for treated animals. The treatment therefore reactivated myelination, which was inhibited by overexpression of PMP22.

Molecular Mechanism of the Correction:

Expression of the PMP22 gene is under the direct control of cAMP, via CREB binding to two sites in the gene promoter located 1.5 kb from the transcription initiation site. In the absence of cAMP, the activity of the schwann specific minimal promoter (300 bp) is inhibited. Treatment with cAMP removes this inhibition and restores expression of the minimal promoter. One of the hypotheses under consideration was that use of an amount of cAMP which on the contrary is reduced might decrease the activity of this promoter and thereby decrease PMP22 overexpression. Furthermore, the severity of the phenotype appeared to depend on the level of overexpression, with a threshold effect. In fact, 70% overexpression was not pathogenic while 100% overexpression (CMT1A patients) was. In the context of the present invention, the inventors tested the action of vitamin C on the endogenous cAMP pool and found that the reduction of said pool led to a reduction in PMP22 expression, so that the level thereof fell below the threshold of pathogenicity. To test this hypothesis, animals treated for three months with vitamin C and placebo-treated animals from the same litter were sacrificed. The sciatic nerves were harvested, RNA was extracted and expression levels were measured by real-time PCR with the help of primers specific for the human transcript. The results show that the level of PMP22 expression was reduced after vitamin C treatment. The sciatic nerve from treated mice contained eight times less PMP22 messenger RNA than that of placebo mice; 18S RNA was used as control.

Thus, vitamin C at least partially corrects the locomotor pathology of CMT mice, probably by decreasing the level of PMP22 expression. As vitamin C happens to be well known and its pharmacodynamics and toxicity (low) have long been established, phase III clinical trials with this molecule could be envisioned to help meet the need for a treatment, expressed by the many patients who suffer from this pathology.

EXAMPLE 1

A scored effervescent tablet contains approximately:

| INGREDIENTS | UNIT FORMULA (mg) | | |
|---|---|---|---|
| Ascorbic acid | 250 | 1000 | 5000 |
| Citric acid | 300 | 1200 | 6000 |

-continued

| INGREDIENTS | UNIT FORMULA (mg) | | |
|---|---|---|---|
| Sodium bicarbonate | 150 | 600 | 3000 |
| Anhydrous sodium carbonate | 50 | 200 | 1000 |
| Sodium citrate | 1 | 4 | 20 |
| Sweetener | 5 | 20 | 100 |
| Flavoring | 20 | 80 | 400 |
| Coloring agent | 10 | 40 | 200 |
| Purified water | qs | qs | qs |

EXAMPLE 2

A solution for injection contains approximately:

| INGREDIENTS | UNIT FORMULA (mg) |
|---|---|
| Ascorbic acid | 500 |
| Sodium phosphate monobasic, dihydrate | qs pH = 6.0 |
| Hydrochloric acid | qs pH = 6.0 |
| Water for injections | qs 5 ml |

The invention claimed is:

1. A method for the treatment of Charcot-Marie-Tooth disease comprising administering to a subject affected by or presenting a risk of developing such disease, a composition consisting essentially of a therapeutically effective amount of at least one therapeutically active ingredient selected from the group consisting of ascorbic acid, ascorbyl palmitate, dipalmitate L-ascorbate, a glycosylated ascorbic acid, a mannosylated ascorbic acid, a fructosylated ascorbic acid, a fucosylated ascorbic acid, a galactosylated ascorbic acid, a N-acetylglucosaminated ascorbic acid, a N-acetylmuramic ascorbic acid, a metal salt of phosphorylated ascorbic acid, an alkaline metal ascorbyl phosphate, an alkaline earth metal ascorbyl phosphate, a transition metal ascorbyl phosphate, an ascorbyl sulphate, ascorbyl-2 glucoside, 2-O-alpha-D-glucopyranosyl ascorbic acid, 6-O-beta-D-galactopyranosyl L-ascorbic acid, and magnesium ascorbyl phosphate.

2. The method according to claim 1, wherein said Charcot-Marie-Tooth disease is type I Charcot-MarieTooth disease (CMTI).

3. The method according to claim 1, wherein the ascorbic acid is selected from a natural vitamin C and a synthetic vitamin C.

4. The method according to claim 1, wherein the at least one therapeutically active ingredient is administered to a human in need of such treatment in unit doses comprising from 1 g to 6 grams of the at least one therapeutically active ingredient.

* * * * *